US009039658B2

(12) United States Patent
Adams et al.

(10) Patent No.: US 9,039,658 B2
(45) Date of Patent: May 26, 2015

(54) MEDICAL CATHETER ASSEMBLY INCLUDING A BALLOON BOLSTER

(71) Applicant: Boston Scientific Scimed, Inc., Maple Grove, MN (US)

(72) Inventors: Mark L. Adams, Sandy, UT (US); Kim Dang, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/036,831

(22) Filed: Sep. 25, 2013

(65) Prior Publication Data

US 2014/0025032 A1 Jan. 23, 2014

Related U.S. Application Data

(63) Continuation of application No. 13/419,765, filed on Mar. 14, 2012, now Pat. No. 8,562,560, which is a continuation of application No. 11/975,680, filed on Oct. 20, 2007, now Pat. No. 8,157,765.

(60) Provisional application No. 60/853,136, filed on Oct. 20, 2006.

(51) Int. Cl.
*A61M 31/00* (2006.01)
*A61M 29/00* (2006.01)
*A61J 15/00* (2006.01)
*A61M 25/04* (2006.01)

(52) U.S. Cl.
CPC .......... *A61J 15/0042* (2013.01); *A61J 15/0015* (2013.01); *A61J 15/0057* (2013.01); *A61M 25/04* (2013.01); *A61J 15/0092* (2013.01); *A61J 15/0065* (2013.01)

(58) Field of Classification Search
CPC .............. A61J 15/0015; A61J 15/0042; A61J 15/0061; A61J 15/0038; A61J 15/0073; A61J 15/0034; A61J 15/0069; A61J 15/0057; A61J 15/0026; A61J 15/003; A61J 15/00; A61J 15/0053; A61M 25/04; A61M 2025/0233; A61M 25/005; A61M 2039/0255; A61M 39/0247; A61B 17/3415; A61B 2017/3486
USPC ....................................... 604/96.01
See application file for complete search history.

(56) References Cited

U.S. PATENT DOCUMENTS

2004/0116894 A1* 6/2004 DeLegge ...................... 604/500
2006/0229553 A1* 10/2006 Hammack et al. .......... 604/96.01

* cited by examiner

Primary Examiner — Jason Flick
(74) Attorney, Agent, or Firm — Fay Kaplun & Marcin, LLP (57) ABSTRACT

A medical catheter assembly including either a reinforced balloon bolster or the combination of a balloon bolster and a wire-basket bolster. According to one embodiment, the medical catheter assembly is a low-profile replacement PEG device comprising a feeding tube, an external bolster, an end cap and an internal bolster. The internal bolster comprises a first expandable structure and a second expandable structure. In one embodiment, the first expandable structure is a balloon and the second expandable structure comprises reinforcing members. In another embodiment, the first expandable structure is a balloon and the second expandable structure is a wire basket bolster. The feeding tube has a feeding lumen and an inflation lumen, extending parallel longitudinally. The external bolster is fixed to the external end of the feeding tube and has a feeding lumen aligned with that of the tube and an inflation lumen aligned with that of the tube.

15 Claims, 8 Drawing Sheets

MEDICAL CATHETER ASSEMBLY INCLUDING A BALLOON BOLSTER

CROSS-REFERENCE TO RELATED APPLICATIONS

The present application is a Continuation of U.S. patent application Ser. No. 13/419,765 filed on Mar. 14, 2012, now U.S. Patent No. 8,562,560, which is a Continuation of U.S. patent application Ser. No. 11/975,680 filed Oct. 20, 2007, now U.S. Patent No. 8,157,765; which claims priority to U.S. Provisional patent application Ser. No. 60/853,136 filed on Oct. 20, 2006. The entire disclosure of these applications/patents are expressly incorporated herein by reference.

BACKGROUND OF THE INVENTION

The present invention relates generally to medical catheter assemblies of the type including a medical catheter and a balloon bolster disposed at the internal end of the medical catheter for retaining said end of said medical catheter within a patient and relates more particularly to a novel such medical catheter assembly.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. (A less common approach involves jejunostomy, i.e., the creating of a feeding tract or stoma leading into the patient's jejunum.) Feeding is then typically performed by administering food through a catheter or feeding tube that has been inserted into the feeding tract, with one end of the feeding tube extending into the stomach and being retained therein by an internal anchor or bolster and the other end of the feeding tube extending through the abdominal wall and terminating outside the patient.

Although gastrostomies were first performed surgically, most gastrostomies are now performed using percutaneous endoscopy and result in the implantation in the patient of a feeding tube/internal bolster assembly (said feeding tube/internal bolster assembly also commonly referred to as a percutaneous endoscopy gastrostomy (PEG) device). Two of the more common percutaneous endoscopic techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, one end of an endoscope is intubated (i.e., inserted) into a patient's mouth and is passed through the esophagus into the stomach. After distension of the stomach by inflation, an entry site on the abdomen is identified using the endoscope for transillumination, and an incision is made by passing the tip of a needle coupled to an outer cannula through the abdominal and stomach walls and into the stomach. One end of the outer cannula remains outside of the body and acts as a stop to limit insertion of the needle and outer cannula into the stomach. A snare is inserted into the stomach via the endoscope and is looped over the inserted end of the needle. The snare is then "walked" up the needle until the outer cannula is snared. The snared cannula is then pulled externally to tack the cannula to the stomach and, in turn, to secure the stomach wall to the abdominal wall. The needle is then removed from the patient while keeping the cannula in place. A first end of a flexible guidewire (also known in the art as a "pushwire") is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and typically form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the stomach wall. The guidewire is then removed from the patient. The clinician then re-intubates the patient with the endoscope and uses an optical channel in the endoscope to inspect whether the internal bolster is properly seated in the stomach.

If the internal bolster is properly placed against the stomach wall, a length of the externally-extending portion of the implanted gastrostomy feeding tube is then typically cut and removed from the implanted tube to reduce the externally-extending portion of the tube to a desired length (typically about 4-6 inches). (The removal of the leading end of the gastrostomy feeding tube also results in the removal of the dilator, which is connected thereto.) An external bolster is typically secured to the remaining externally-extending portion of the feeding tube to engage the abdomen in such a way as to prevent longitudinal movement of the feeding tube into the stomach. Additionally, a "Y-port" adapter is typically attached to the external end of the feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

The pull method is similar in some respects to the above-described push method, the pull method differing from the push method in that, after the cannula is snared and the needle is removed therefrom, a looped first end of a suture (also known in the art as a "pullwire") is inserted through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly typically comprising a gastrostomy feeding tube having an internal bolster integrally formed at its trailing end and a plastic fitting attached to its leading end. The plastic fitting typically has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop. Using the second end of the suture, the pull-type catheter implanting assembly is then pulled retrograde through the patient until the gastrostomy feeding tube emerges from the abdomen of the patient and the internal bolster engages the stomach wall of the patient. Next, as is the case in the push method, the clinician then re-intubates the patient with the endoscope in order to visually inspect the placement of the internal bolster within the stomach. If the bolster is properly seated in the stomach, the externally-extending portion of the implanted gastrostomy feeding tube is then typically cut to a desired length and one or more of an external bolster, a Y-port and a clamp are attached to the feeding tube.

In addition to the above-described endoscopic techniques for implanting PEG devices, there also exist direct percutaneous techniques.

Although PEG devices of the type described above work well for their intended purpose, such devices tend to wear out over time and/or do not suit the lifestyle of more active patients as the several inches length of tubing that extends externally can be unwieldy, difficult to conceal and susceptible to being inadvertently pulled on. Consequently, various types of replacement PEG devices have been devised to replace initially-implanted PEG devices. Some of these replacement PEG devices are often referred to as "low-profile" in that they are considerably more compact externally than the above-described initially-implanted PEG devices and, thus, are particularly well-suited for active patients. Other replacement PEG devices are often referred to as "standard-profile" in that they are less compact than "low-profile" PEG devices.

Many replacement PEG devices, whether "low-profile" or "standard-profile," use an inflatable balloon as an internal bolster to retain the inserted end of the feeding tube within a patient's stomach. To implant such a device in a patient, the end of the tube carrying the balloon is inserted through the stoma with the inflatable balloon in a deflated state, and the balloon is then inflated, typically using a needle-less syringe or the like. The balloon may be inflated with air or, more preferably, is inflated with a sterile, biologically compatible liquid, such as a saline solution. To remove the implanted device from a patient, the balloon is deflated, and the tube is then withdrawn from the stoma. Examples of replacement PEG devices having an inflatable balloon bolster are disclosed in the following U.S. patents and published U.S. patent applications, all of which are incorporated by reference: U.S. Pat. No. 4,685,901, inventor Parks, which issued Aug. 11, 1987; U.S. Pat. No. 5,342,321, inventor Potter, which issued Aug. 30, 1994; U.S. Pat. No. 5,836,924, inventors Kelliher et al., which issued Nov. 17, 1998; U.S. Pat. No. 5,860,952, inventor Quinn, which issued Jan. 19, 1999; U.S. Pat. 5,997,503, inventors Willis et al., which issued Dec. 7, 1999; U.S. Pat. No. 6,077,243, inventor Quinn, which issued Jun. 20, 2000; U.S. Pat. No. 6,019,746, inventors Picha et al., which issued Feb. 1, 2000; U.S. Pat. No. 6,264,631, inventors Willis et al., which issued Jul. 24, 2001; U.S. Pat. No. 6,916,307, inventors Willis et al., which issued Jul. 12, 2005; and U.S. Patent Application Publication No. US 2004/0147874, inventors Kliem et al., which was published Jul. 29, 2004.

One shortcoming of PEG devices having a balloon bolster is that the balloon bolster has a tendency to fail over time. As can be appreciated, failure of the bolster can lead to the device falling out of the patient, an occurrence that is not desired.

SUMMARY OF THE INVENTION

In one embodiment, the invention provides a novel medical catheter assembly of the type having a balloon bolster.

In another embodiment, the invention provides a medical catheter assembly as described above that overcomes at least some of the shortcomings in connection with existing medical catheter assemblies of the type having a balloon bolster.

Therefore, according to one aspect of the invention, there is provided a medical catheter assembly, said medical catheter assembly comprising (a) a medical catheter; and (b) an expandable bolster disposed at a first end of said medical catheter, said expandable bolster comprising a ribbed or reinforced balloon. The ribbed or reinforced balloon may comprise a flexible sleeve having embedded therein at least one of the following: at least one linear reinforcing stay, at least one circumferential reinforcing member, at least one helical reinforcing member and an expandable wire mesh tube.

According to another aspect of the invention, there is provided a medical catheter assembly, said medical catheter assembly comprising (a) a medical catheter; (b) a first expandable bolster disposed at a first end of said medical catheter; and (c) a second expandable bolster disposed at said first end of said medical catheter. In one embodiment, the first expandable bolster may be a balloon bolster, and the second expandable bolster may be a wire-basket bolster, the wire-basket bolster being disposed within the balloon bolster.

According to yet another aspect of the invention, there is provided a method of securing a device, the method comprising actuating a first bolster and actuating a second bolster wherein the second bolster serves to maintain security upon failure of the first bolster.

For purposes of the present specification, various relational terms like "top," "bottom," "internal," "external," "proximal" and "distal" are used to describe the present invention when said invention is positioned in or viewed from a given orientation. It is to be understood that, by altering the orientation of the invention, certain relational terms may need to be adjusted accordingly.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
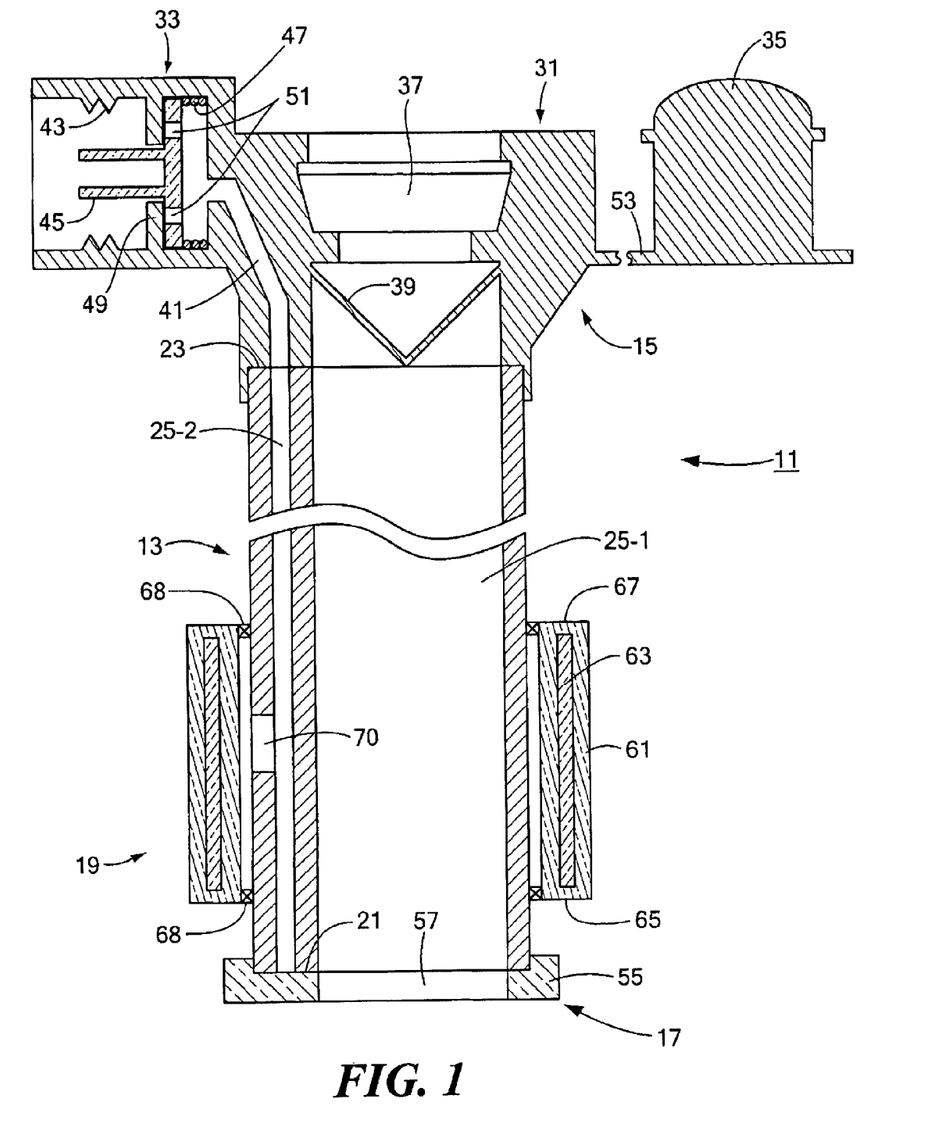
FIG. 1 is a section view of a first embodiment of a medical catheter assembly constructed according to the teachings of the present invention, the medical catheter assembly including an internal bolster that is shown in an unexpanded state.
Figure 2:
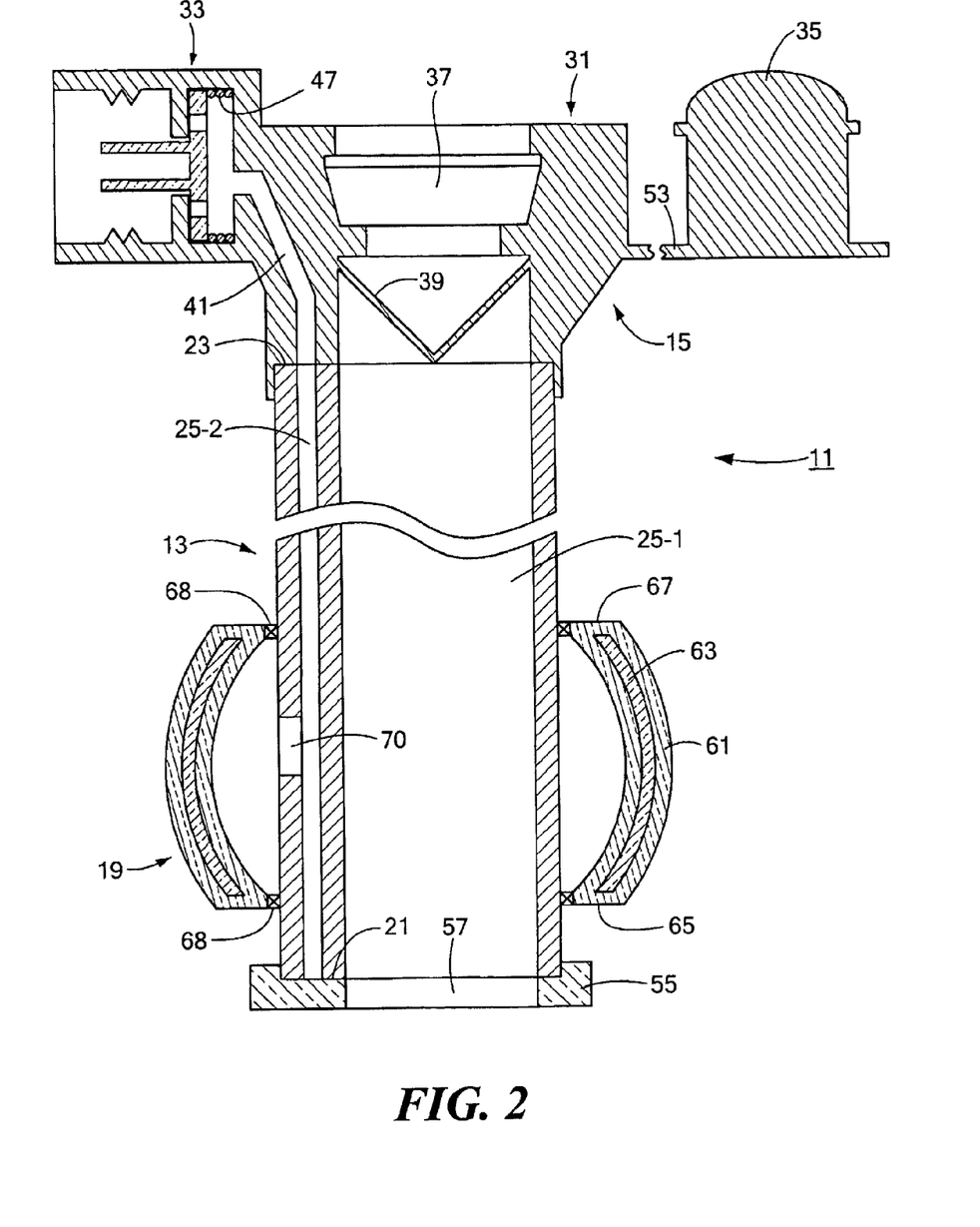
FIG. 2 is a section view of the medical catheter assembly of FIG. 1, the internal bolster being shown in an unexpanded state.
Figure 3:
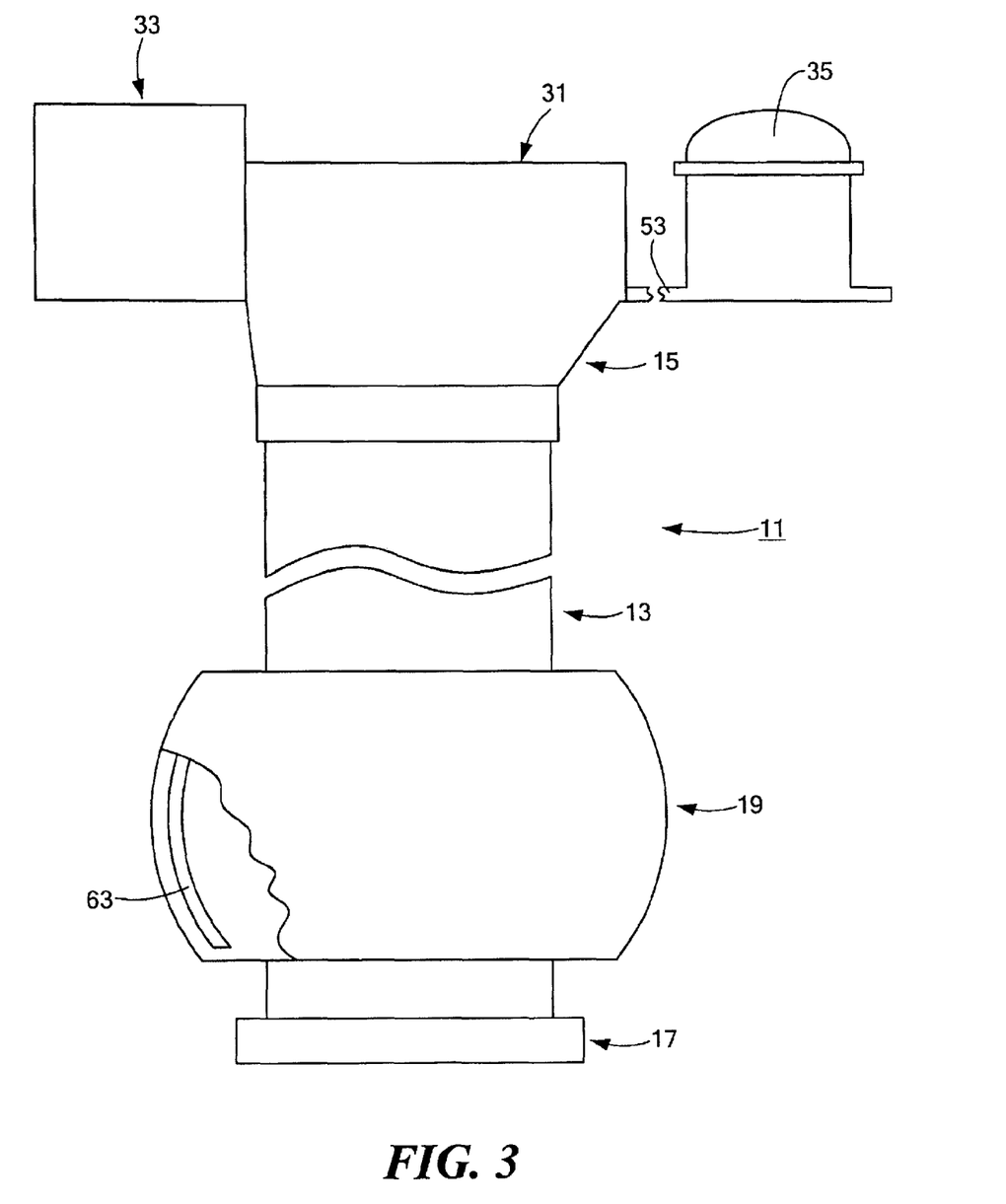
FIG. 3 is a side view, broken away in part, of the medical catheter assembly of FIG. 1, the internal bolster being shown in an expanded state.

Referring now to FIGS. 1 through 3, there are shown various views of a first embodiment of a medical catheter assembly constructed according to the teachings of the invention, said medical catheter assembly being represented generally by reference numeral 11.

Assembly 11, which, in the present embodiment, may be a low-profile replacement PEG device, may comprise a feeding tube 13, an external bolster 15, an end cap 17 and an internal bolster 19.

Feeding tube 13 may be an elongated, flexible, tubular member, comprising a suitable medical grade silicone, polyurethane or any other suitably flexible biocompatible polymer or structure (such as a woven tube or the like). Feeding tube 13 may be shaped to include an internal end 21, an external end 23, and a pair of longitudinal lumina 25-1 and 25-2, lumina 25-1 and 25-2 extending in a parallel fashion from internal end 21 to external end 23. Lumen 25-1 may be considerably greater in diameter than lumen 25-2, and as will become apparent below, lumen 25-1 may be used to convey food and/or medications to a patient whereas lumen 25-2 may be used to convey fluids to and from internal bolster 19 for its inflation and deflation, respectively.

External bolster 15, which in some embodiments may be fixedly mounted on external end 23 of feeding tube 13, may be a unitary structure, made of a suitable medical grade silicone, polyurethane or any other suitably flexible biocompatible polymer or structure. Bolster 15 may be shaped to comprise a feeding port 31, an inflation port 33 and a plug 35. Feeding port 31 may include a feeding lumen 37, feeding lumen 37 being aligned with lumen 25-1 and may be adapted to receive a feeding tip (not shown) of a conventional device used to dispense food and/or medications into a PEG device. An anti-reflux valve 39, which, in the present embodiment, may be in the form of an integrally formed duckbill valve, may be disposed within lumen 37 and may be appropriately positioned therewithin to be opened by the full insertion of a feeding tip into lumen 37.

Inflation port 33 may include an inflation lumen 41, and inflation lumen 41 may be aligned with lumen 25-2 of feeding tube 13. An internal thread 43 may project into lumen 41 near the external end of lumen 41 so that lumen 41 may matingly receive the externally-threaded tip of a needle-less syringe. A check valve, which, in the present embodiment, may comprise a plunger 45 and a spring 47, may be disposed within lumen 41. In the absence of a syringe being inserted into lumen 41, spring 47 biases plunger 45 against an apertured wall 49, thereby preventing fluid flow through apertured wall 49. On the other hand, when a syringe is inserted into lumen 41, plunger 45 is displaced by syringe towards feeding tube 13 so that fluid is permitted to flow through apertured wall 49. A plurality of transverse openings 51 may be provided in plunger 45 to permit fluid to flow through plunger 45 as well as through apertured wall 49. It should be noted that the check valve is not limited to the foregoing structure and may take the form of any commonly known valve including a ball/spring, flapper, duckbill, etc.

Plug 35, which may be tethered to feeding port 31 by a flexible strap 53, may be appropriately sized to sealably, yet removably, fit into the external end of feeding lumen 37.

End cap 17, which may be a unitary structure made of a suitable medical grade silicone, polyurethane or any other suitably flexible biocompatible polymer or structure, may be fixedly mounted on internal end 21 of feeding tube 13. End cap 17 may comprise an end wall 55, end wall 55 sealing the internal end of lumen 25-2. A transverse opening 57 may be provided in end wall 55, and opening 57 may be aligned with lumen 25-1 and matching lumen 25-1 in diameter so that the contents of lumen 25-1 may flow freely through the internal end of lumen 25-1.

Internal bolster 19 may comprise a flexible sleeve 61 and a plurality of reinforcing members 63. Reinforcing members 63 may be embedded within sleeve 61. Sleeve 61, which may be made of an expandable membrane or material, such as a suitable medical grade silicone, polyurethane or any other suitably flexible biocompatible polymer or structure, may be appropriately dimensioned to fit tightly over tube 13, with the internal end 65 of sleeve 61 and the external end 67 of sleeve 61 being securely bonded to tube 13 by a suitable adhesive 68 or by melting. The intermediate portion of sleeve 61, which may not be bonded to tube 13, may lie over an aperture 70 in tube 13, aperture 70 being in fluid communication with lumen 25-2. In this manner, sleeve 61 may be expanded like a conventional balloon bolster by the introduction of fluids passing from lumen 25-2 through opening 70 and against sleeve 61. Reinforcing members 63, which may be linear ribs or stays made of, for example, metals, polymeric materials, elastomeric materials or combinations thereof, may be embedded within sleeve 61, with reinforcing members 63 being spaced apart equidistantly and may be oriented parallel to the length of sleeve 61 or at some other angle relative to the length of sleeve 61. Alternatively, reinforcing members 63 may be circumferential reinforcements oriented perpendicular to the length of sleeve 61 or at some other angle relative to the length of sleeve 61. Alternatively, reinforcing members 63 may include a combination of linear members and circumferential members. (Although two reinforcing members 63 are shown in the present embodiment, it can be appreciated that there could be as few as one reinforcing member 63 or more than two reinforcing members 63.)

Internal bolster 19 may be constructed by a process in which sleeve 61 and reinforcing members 63 are co-extruded. In such a case, the ends of reinforcing members 63 may be covered thereafter with additional sleeve material so that no portion of reinforcing member 63 is exposed. Alternatively, reinforcing members 63 may be sandwiched between two sheets of material that together form sleeve 61.

Reinforcing members 63 may have sufficient flexibility so that, as sleeve 61 is expanded or deflated, reinforcing members 63 assume a corresponding shape. However, at the same time, reinforcing members 63 may have sufficient rigidity so that, if sleeve 61 is expanded, for example, with a liquid, and then suffers a pinhole leak or other non-catastrophic rupture, reinforcing members 63 substantially maintain their shape, keeping the internal end of assembly 11 within the patient on a temporary basis and allowing the patient to seek treatment from a medical professional. (Assembly 11 additionally may include some means, such as an indicator in inflation port 33, to indicate an unexpected loss in inflation pressure in bolster 19.) The medical professional may then pull on assembly 11 until the withdrawal force exceeds the retention force provided by reinforcing members 63.

To implant assembly 11 in a patient, one may begin with bolster 19 in an unexpanded state (see FIG. 1) and may insert into the patient via an existing stoma substantially all of assembly 11, except for external bolster 15. Next, one may connect a needle-less syringe to inflation port 33 and may dispense a fluid (preferably a liquid, such as saline solution or sterile water) into inflation lumen 41 until inflation bolster 19 is expanded to a desired extent (see FIGS. 2 and 3). One may then remove the needle-less syringe from inflation port 33.

Once assembly 11 has been implanted in a patient in the above manner, one may deliver food and/or medications to the patient through feeding port 31 in the conventional manner. When feeding port 31 is not in use, one may seal feeding port 31 with plug 35.

To remove assembly 11 from a patient, one may connect a needle-less syringe or the like to feeding port 31 and then may withdraw a sufficient quantity of fluid from within bolster 19 until bolster 19 shrinks to a sufficiently compact size to permit the withdrawal of assembly 11 from the patient.

It should be understood that, although assembly 11 has been described herein as a replacement PEG device, assembly 11 is not limited to gastric applications nor is it limited to feeding applications. Moreover, assembly 11 is not limited to use as replacement device and may be used as an initial placement device. Furthermore, assembly 11 may be modified to be a standard-profile device, instead of a low-profile device, without departing from the present invention.

In other embodiments (not shown), bolster 19 may include a multi-layer balloon structure, a second or reinforcing balloon structure located inside a first balloon structure, or a balloon structure with a reinforcing covering.

Figure 4:
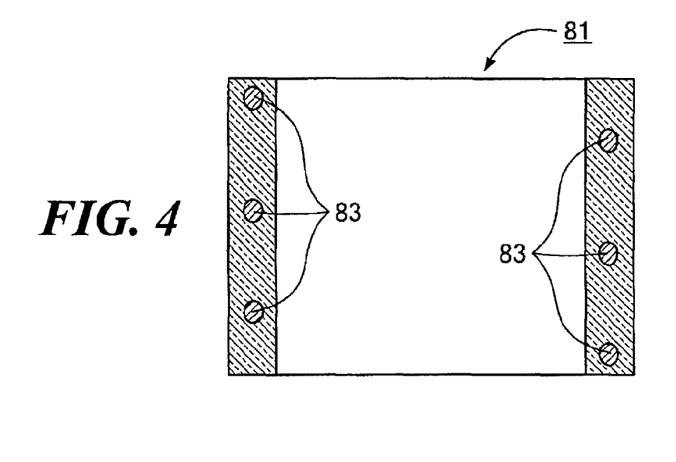
FIG. 4 is a section view of a first alternate internal bolster for use with the medical catheter assembly of FIG. 1.

Referring now to FIG. 4, there is shown a section view of a first alternate internal bolster, said first alternate internal bolster being represented by reference numeral 81.

Internal bolster 81, which may be used instead of internal bolster 19 with the remainder of assembly 11, is similar in most respects to internal bolster 19, the principal difference between the two internal bolsters being that internal bolster 81 may include a single helical reinforcing member 83, instead of a plurality of linear reinforcing members 63. Reinforcing member 83 may be similar in structure to reinforcing members 63 or may be made of a metal or polymer wire or a coil.

Figures 5, 6:
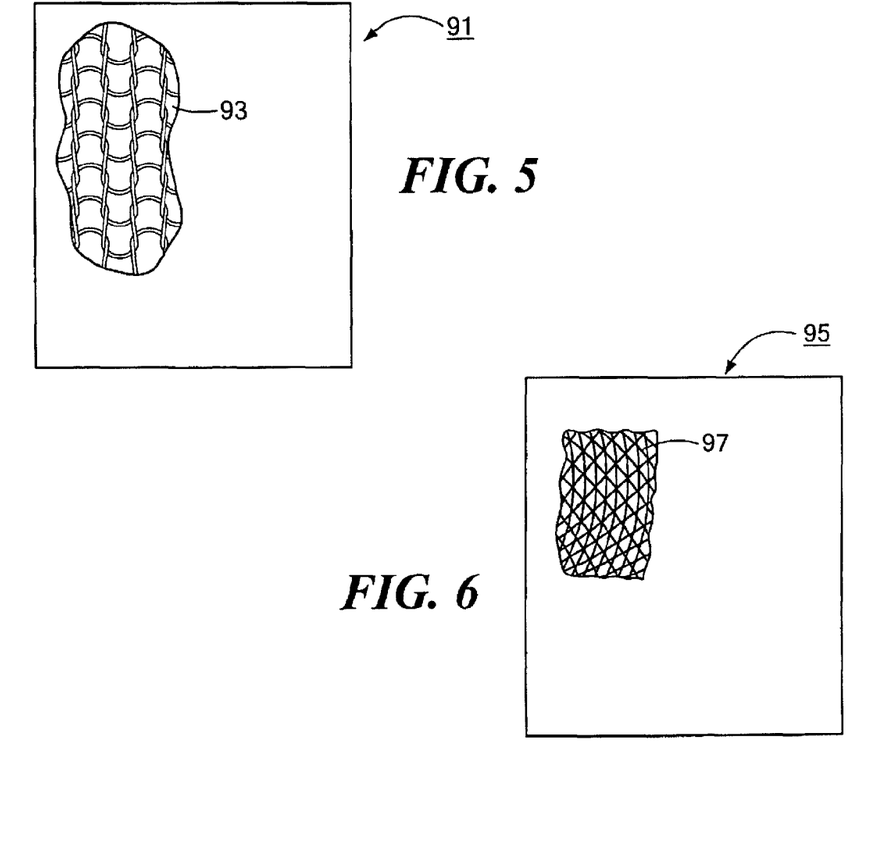
FIG. 5 is a side view, broken away in part, of a second alternate internal bolster for use with the medical catheter assembly of FIG. 1.
FIG. 6 is a side view, broken away in part, of a third alternate internal bolster for use with the medical catheter assembly of FIG. 1.

Referring now to FIG. 5, there is shown a side view, broken away in part, of a second alternate internal bolster, said second alternate internal bolster being represented by reference numeral 91.

Internal bolster 91, which may be used instead of internal bolster 19 with the remainder of assembly 11, is similar in most respects to internal bolster 19, the principal difference between the two internal bolsters being that internal bolster 91 may include an expandable wire mesh tube 93 (such as in a balloon-expandable intravascular stent), instead of a plurality of linear reinforcing members 63. This tube may take many forms including a knitted or laser cut tube, for example, and is not limited to the particular type of tube shown.

Referring now to FIG. 6, there is shown a side view, broken away in part, of a third alternate internal bolster, said third alternate internal bolster being represented by reference numeral 95.

Internal bolster 95, which may be used instead of internal bolster 19 with the remainder of assembly 11, is similar in most respects to internal bolster 19, the principal difference between the two internal bolsters being that internal bolster 95 may include a woven, expandable wire mesh tube 97 (such as in a balloon-expandable intravascular stent), instead of a plurality of linear reinforcing members 63.

Referring now to FIGS. 7 through 10, there are shown various views of a second embodiment of a medical catheter assembly constructed according to the teachings of the invention, said medical catheter assembly being represented generally by reference numeral 101.

Figure 7:
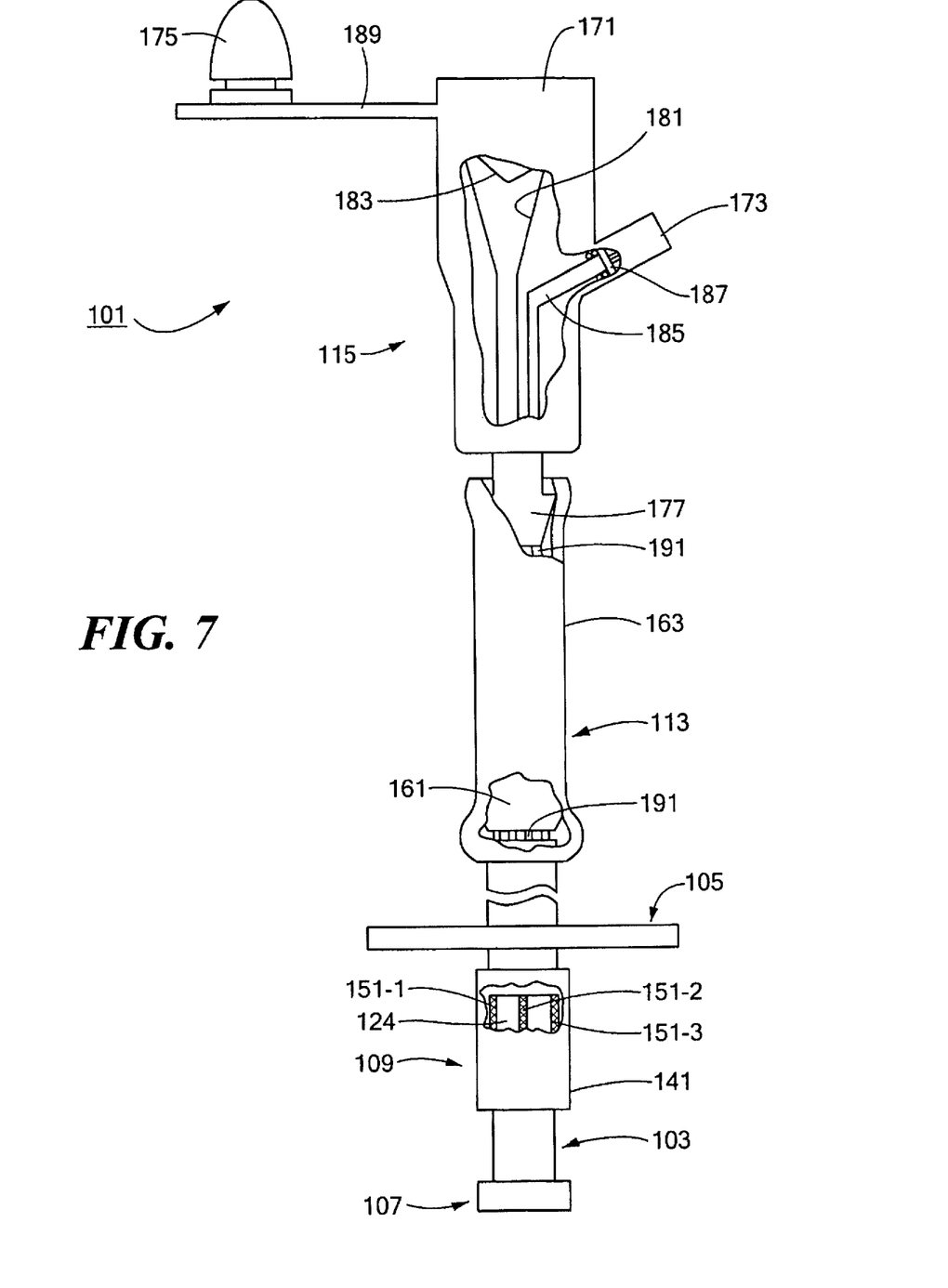
FIG. 7 is a side view of a second embodiment of a medical catheter assembly constructed according to the teachings of the present invention.
Figure 8:
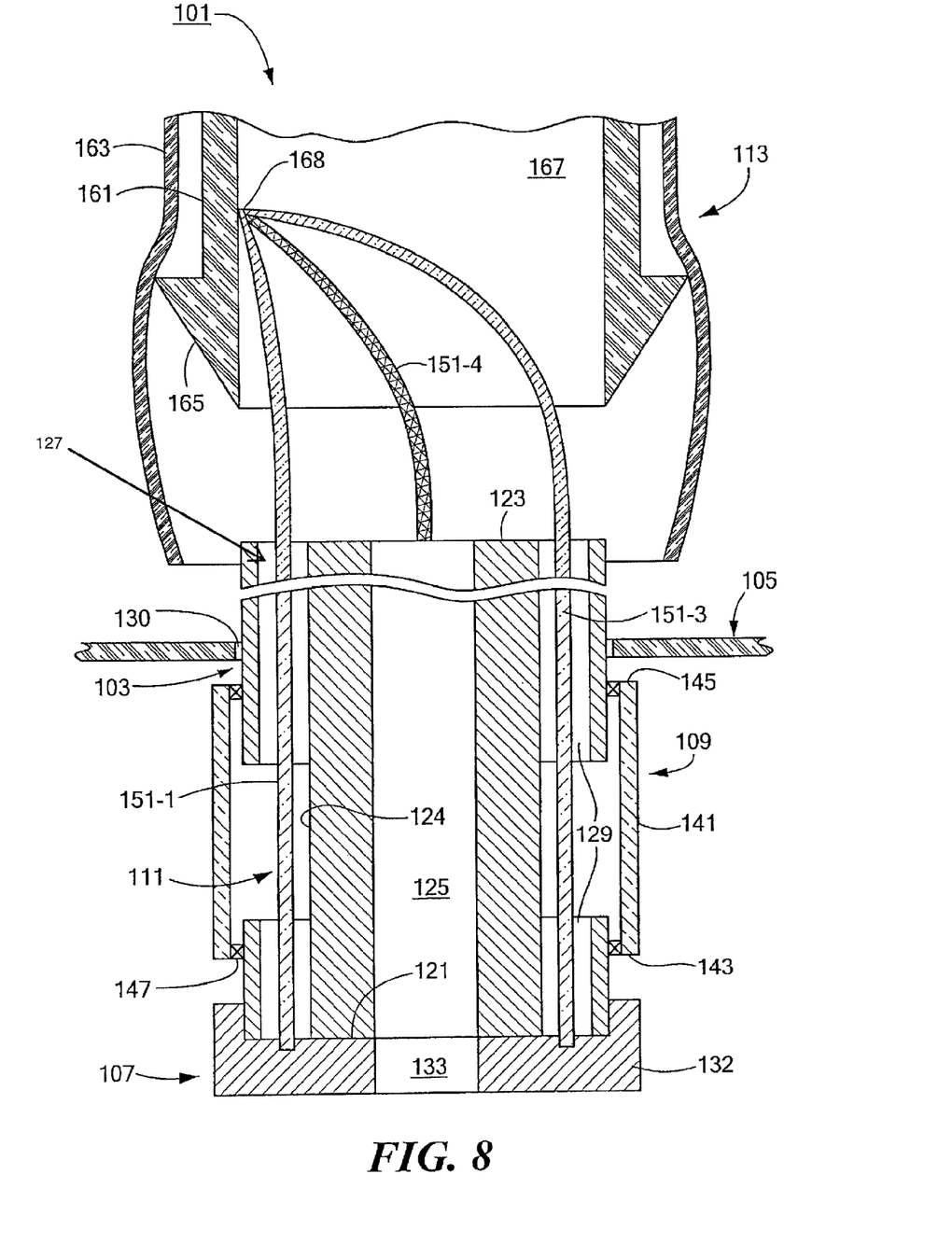
FIG. 8 is a fragmentary perspective view of the medical catheter assembly of FIG. 7, with each of the balloon bolster and the wire basket bolster of the medical catheter assembly being shown in an unexpanded state.

Assembly 101, which, in the present embodiment, may be a standard-profile replacement PEG device, may comprise a feeding tube 103, an external bolster 105, an end cap 107, a balloon bolster 109, a wire-basket bolster 111 (seen best in FIGS. 8 and 9), a wire-basket actuation assembly 113, and a Y-port 115.

Feeding tube 103 may be an elongated, flexible, tubular member made, for example, of a suitable medical grade silicone, polyurethane or other suitably flexible biocompatible polymer or structure. Feeding tube 103 may have a uniform outer diameter along its entire length, except for an intermediate waist portion 124 of narrowed outer diameter, and may be shaped to include an internal end 121, an external end 123, a feeding lumen 125, an inflation lumen 127 and a plurality of wire lumina 129. Feeding lumen 125, which may be considerably greater in diameter than inflation lumen 127 and wire lumina 129, may be centrally disposed and may extend longitudinally between internal end 121 and external end 123. Inflation lumen 127 and wire lumina 129 may not be present in intermediate waist portion 124 but elsewhere extend parallel to feeding lumen 125 and be spaced around the periphery of feeding lumen 125. Wire lumina 129 may be equidistantly spaced apart from one another.

External bolster 105 may be a flexible, unitary member made, for example, of a suitable medical grade silicone, polyurethane or other suitably flexible biocompatible polymer or structure. In the present embodiment, external bolster 105 may be a generally disc-shaped structure having a central opening 130 into which tube 103 is inserted and may be securely retained by a friction-fit; however, it should be understood that external bolster 105 could be replaced with a variety of different types of external bolsters, including many types of conventional external bolsters, without departing from the present invention.

End cap 107, which may be a unitary structure made, for example, of a suitable medical grade silicone, polyurethane or other suitably flexible biocompatible polymer or structure, may be fixedly mounted on internal end 121 of feeding tube 103. End cap 107 may comprise an end wall 132, end wall 132 sealing the internal ends of inflation lumen 127 and wire lumina 129. (Alternatively, this could be done with melting, thereby obviating the need for end cap 107.) A transverse opening 133 may be provided in end wall 132, opening 133 being aligned with feeding lumen 125 and matching lumen 125 in diameter so that the contents of lumen 125 may flow freely through the internal end of lumen 125.

Balloon bolster 109 may comprise a flexible sleeve 141. Sleeve 141, which may be made, for example, of a suitable medical grade silicone, polyurethane or other suitably flexible biocompatible polymer or structure, may be appropriately dimensioned to fit tightly over tube 103, with the internal end 143 of sleeve 141 and the external end 145 of sleeve 141 being securely bonded to tube 103 by a suitable adhesive 147 and with the intermediate portion of sleeve 141, which is not bonded to tube 103, extending over intermediate waist portion 124 of tube 103. In this manner, sleeve 141 may be expanded like a conventional balloon bolster by the introduction of fluids passing from inflation lumen 127 through waist portion 124 and against sleeve 141.

Wire-basket bolster 111 may comprise a plurality of flexible wires, for example, wires 151-1 through 151-4, each of wires 151-1 through 151-4 preferably being a braided wire, more preferably being a braided wire made of a material having shape-memory, elastic or super-elastic properties. For example, nitinol may be used to form wires 151-1 through 151-4; alternatively, other suitable metals, polymers or combinations may be used. It should be noted that the invention is not limited to the number of flexible wires that may comprise bolster 111. Each wire 151 may extend entirely through a corresponding wire lumen 129, with the internal ends of wires 151 being fixed to end wall 132 of end cap 107 and the external ends of wires 151 being bundled together and fixed to wire basket actuation assembly 113. In this manner, when wire-basket actuation assembly 113 is moved in the direction of end cap 107, wires 151 are forced to bow outwardly through intermediate waist portion 124, thereby forming a wire-basket bolster. Thereafter, when wire-basket actuation assembly 113 is moved away from end cap 107, wires 151 return to their straightened states. (By making wires 151 from a material having shape-memory properties, one can bias the return of wires 151 to their straightened states.) In some embodiments, the flexible wires may comprise metals, polymers or combinations thereof. If desired, wires 151 may be made to expand at body temperature or may be made to be biased towards a naturally bowed shape. In either case, the wires could be straightened out by withdrawal of the device.

Wire-basket actuation assembly 113 may comprise a fitting 161 and an elongated tube 163. Fitting 161, which may be a rigid tubular structure preferably made of a medical grade plastic, may be shaped to include a barb 165 and a longitudinal lumen 167, barb 165 being appropriately dimensioned to fix fitting 161 within tube 163 by a friction-fit. The external ends of wires 151 may be coupled together in a bundle 168, bundle 168 being fixed to lumen 167 by a suitable adhesive (not shown). (Instead of being bundled together in the manner shown, the external ends of wires 151 could be connected around the inner circumference of lumen 167 or could be secured to a ring that is, in turn, attached to the inside of lumen 167 or embedded within fitting 161.) Lumen 167 may be appropriately dimensioned to receive external end 123 of tube 103 by a friction-fit. Accordingly, when one wishes to expand wire-basket bolster 111, one may simply slide tube 163 towards tube 103 until tube 103 is securely received in fitting 161. Thereafter, to return wire-basket bolster 111 to its unexpanded state, one may pull tube 163 away from tube 103 until tube 103 is removed from fitting 161 and wires 151 straighten.

Y-port 115 may comprise a feeding port 171, an inflation port 173, a plug 175 and a barbed fitting 177. Feeding port 171 may include a feeding lumen 181, feeding lumen 181 being adapted to receive a feeding tip (not shown) of a conventional device used to dispense food and/or medications into a PEG device. An anti-reflux valve 183, which, in the present embodiment, may be an integrally formed duckbill valve, may be disposed within lumen 181 and may be appropriately positioned therewithin to be opened by the full insertion of a feeding tip into lumen 181. Inflation port 173 may include an inflation lumen 185. A check valve 187, which may be identical in construction to the check valve of assembly 11, may be disposed within inflation lumen 185. Plug 175, which may be tethered to feeding port 173 by a flexible strap 189 or the like, may be appropriately sized to sealably, yet removably, fit into the external end of feeding lumen 181. Barbed fitting 177, which may have separate lumina (not shown) aligned with feeding lumen 181 and inflation lumen 185, may be received, by a friction-fit, for example, within the external end of tube 163. Other fixture methods known in the art are conceivable, such as a screw-fit, snap-fit, etc. A small tube 191 may be inserted at one end in the inflation lumen of barbed fitting 177 and at the other end in inflation lumen 127 of tube 103. In this manner, inflation fluids may be kept separate from feeding materials.

To implant assembly 101 in a patient, one may begin with balloon bolster 109 and wire-basket bolster 111 in their unexpanded states (see FIGS. 7, 8 and 10) and then may insert into the patient via an existing stoma the internal end of assembly 101, with further insertion of assembly 101 being limited by external bolster 105. Next, one may connect a syringe to inflation port 173 and may dispense a fluid (preferably a liquid, such as saline solution or sterile water) into inflation lumen 185 until inflation bolster 109 is expanded to a desired extent. One then may remove the syringe from inflation port 173. Next, one may expand wire-basket bolster 111 by sliding tube 163 towards tube 103 until tube 103 is securely received in fitting 161 (see FIG. 9).

As can be appreciated, because of the presence of wire-basket bolster 111, if balloon bolster 109 fails, the internal end of assembly 101 is still retained within a patient while the patient seeks medical treatment.

Figure 9:
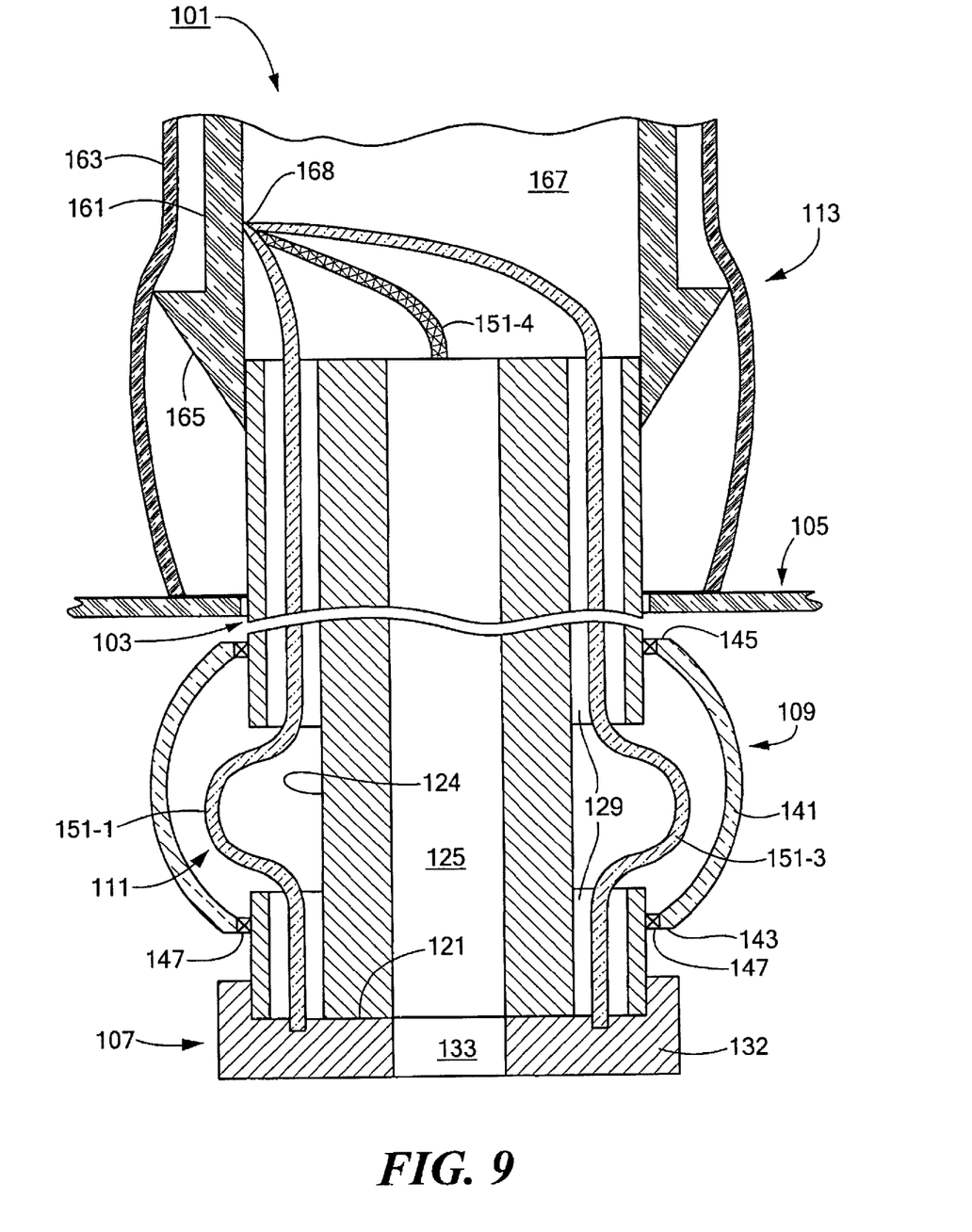
FIG. 9 is a fragmentary section view of the medical catheter assembly of FIG. 7, with each of the balloon bolster and the wire basket bolster of the medical catheter assembly being shown in an unexpanded state.
Figure 10:
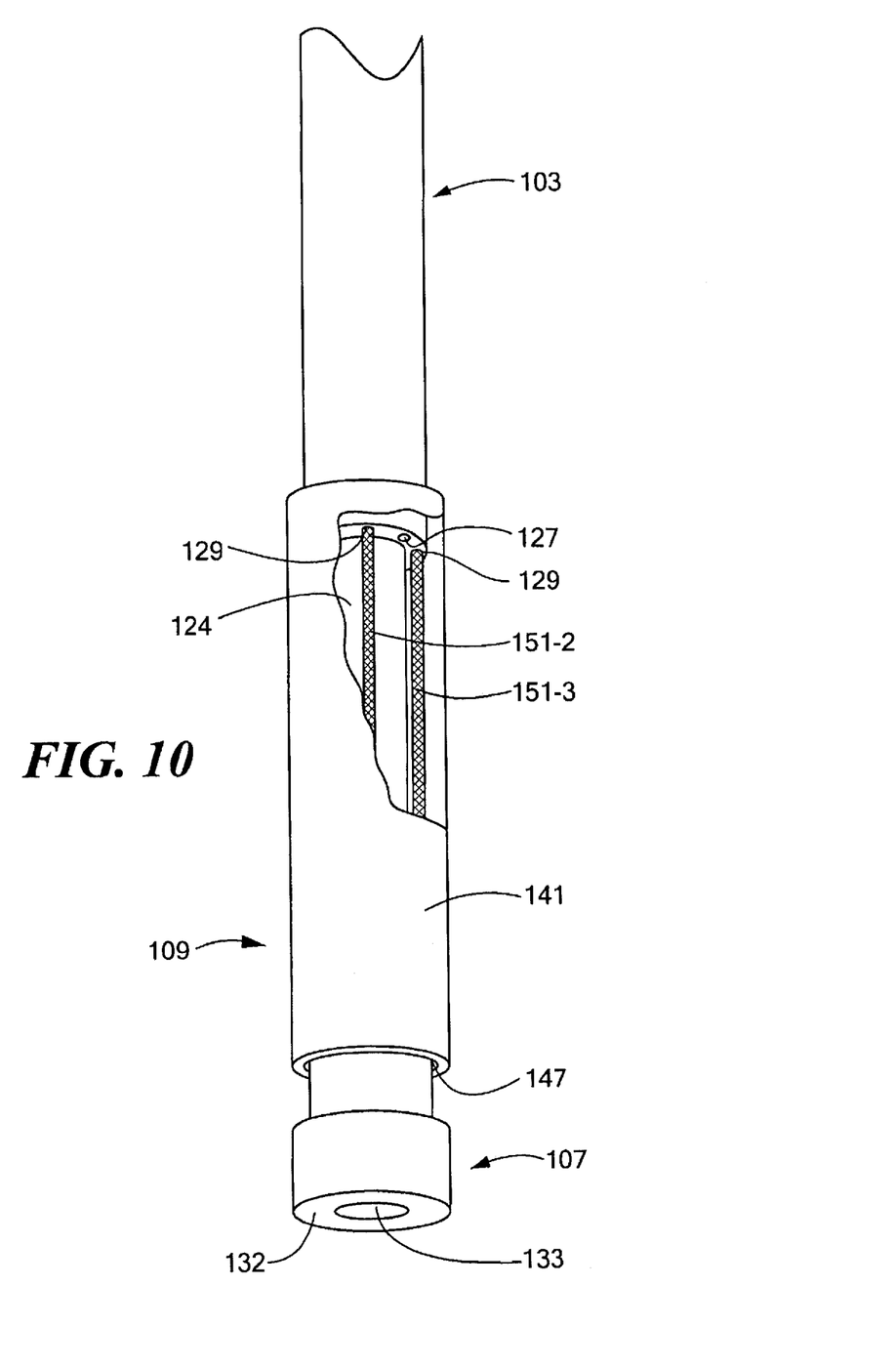
FIG. 10 is a fragmentary section view of the medical catheter assembly of FIG. 7, with each of the balloon bolster and the wire basket bolster of the medical catheter assembly being shown in an expanded state.

It should be noted that, although, in the present embodiment, wire-basket bolster 111, when expanded, does not contact the radially inside surface of balloon bolster 109, wire-basket bolster 111 could be so modified.

Once assembly 101 has been implanted in a patient in the above manner, one may deliver food and/or medications to the patient through feeding port 171 in the conventional manner. When feeding port 171 is not in use, one preferably seals feeding port 171 with plug 175.

To remove assembly 101 from a patient, one may pull tube 163 away from tube 103 until tube 103 is removed from fitting 161 and wires 151 straighten, thereby returning wire-basket bolster 111 to its unexpanded state. Then, one may connect a syringe or the like to feeding port 171 and withdraw a sufficient quantity of fluid from within bolster 109 until bolster 109 shrinks to a sufficiently compact size to permit the withdrawal of assembly 101 from the patient.

It should be understood that, although assembly 101 has been described herein as a replacement PEG device, assembly 101 is not limited to gastric applications nor is it limited to feeding applications. Moreover, assembly 101 is not limited to use as replacement device and may be used as an initial placement device. Furthermore, assembly 101 may be modified to be a low-profile device, instead of a standard-profile device, without departing from the present invention.

It should also be understood that, although wires 151-1 through 151-4 run parallel to lumen 125, wires 151-1 through 151-4 could be helically wrapped around lumen 125 or could be replaced with a single helical coil. Also, although wires 151-1 through 151-4 have a generally uniform cross-section along their respective lengths, wires 151-1 through 151-4 could change in cross-section to optimize the strength of the wire structure.

Actuation of wire-basket bolster 111 is not limited to placement of the proximal tube. It may, for example, be actuated by a separate sliding rod or tube to push down on wires 151-1 through 151-4. It may be actuated by twisting tubes. It may be actuated by inflation of the balloon bolster, which could expand the basket and lock the wires in place (there also being an unlocking mechanism). It may also be actuated with a pull wire to compress the tube.

In another embodiment (not shown), wire-basket bolster 111 may be replaced with a second balloon bolster. Such a second balloon bolster may require a second inflation lumen and second inflation port. Such a second bolster would be situated inside of first bolster although it may be situated proximally or distally thereof as well. In still another embodiment (not shown), wire-basket bolster 111 may be replaced with a malecot bolster.

The embodiments of the present invention recited herein are intended to be merely exemplary and those skilled in the art will be able to make numerous variations and modifications to it without departing from the spirit of the present invention. All such variations and modifications are intended to be within the scope of the present invention.

What is claimed is:

1. A method for placing a feeding tube in a patient, comprising:
   inserting a feeding tube to a target location within one of a stomach and a jejunum of the patient, the feeding tube comprising:
      a catheter having a proximal end, a distal end, and a longitudinal axis;
      a balloon bolster coupled to a distal portion of the catheter; and
      a wire-basket bolster adjacent an inner surface of the balloon bolster;
   inflating the balloon bolster from a first insertion configuration to a first expanded configuration to secure the distal end of the catheter at the target location; and
   after inflating the balloon bolster, moving an actuating mechanism from a first position to a second position such that the wire-basket bolster expands from a second insertion configuration to a second expanded configuration.

2. The method of claim 1, wherein the wire-basked bolster includes a plurality of wires.

3. The method of claim 2, wherein the wires are made of one of a shape-memory material, a superelastic, an elastic material, a metal, a polymer, and a combination thereof.

4. The method of claim 2, wherein the wires are biased toward the second insertion configuration.

5. The method of claim 2, wherein the wires are biased toward the second expanded configuration.

6. The method of claim 2, wherein the wires are coupled to the actuating mechanism one of in a bundle that is coupled using an adhesive, with each wire coupled to an inner circumference of the actuating mechanism, and secured to a ring that is coupled to the actuating mechanism.

7. The method of claim 6, wherein each wire includes a proximal end and a distal end, the proximal end of the wire being coupled to the actuating mechanism, the distal end of the wire being coupled to an end cap coupled to the distal end of the catheter.

8. The method of claim 1, wherein the feeding tube further comprises an external bolster coupled to the catheter and disposed between the balloon bolster and the actuating mechanism.

9. The method of claim 8, wherein the external bolster prevents the actuating mechanism from moving beyond the second position.

10. The method of claim 1, wherein the actuating mechanism includes a fitting shaped and dimensioned to correspond to the proximal end of the catheter, the fitting receiving the proximal end of the catheter in the second position.

11. The method of claim 1, wherein the balloon bolster is made of a silicone, a polyurethane, a biocompatible polymer, and a combination thereof.

12. The method of claim 1, wherein the feeding tube includes a Y-port coupled to a proximal end of the actuating mechanism, the Y-port including a feeding port and an inflation port.

13. The method of claim 12, wherein the feeding port includes a first lumen, the actuating mechanism includes a second lumen, and the catheter includes a third lumen, the first, second, and third lumens being fluidly coupled to one another.

14. The method of claim 12, wherein the inflation port includes an inflation lumen fluidly coupled to the balloon bolster for a fluid to be received therein.

15. The method of claim 1, wherein the wire-basket bolster retains the second expanded configuration when the balloon bolster fails to maintain the securing of the distal end of the catheter at the target location.

* * * * *